(12) United States Patent
Youssefi et al.

(10) Patent No.: US 8,385,618 B2
(45) Date of Patent: Feb. 26, 2013

(54) DETERMINATION AND MONITORING OF LASER ENERGY

(75) Inventors: Gerhard Youssefi, Landshut (DE);
Birgit Lutzenberger, Munich (DE);
Julia Hoff, Munich (DE); Ernst Hegels,
Kirchheim (DE)

(73) Assignee: Technolas Perfect Vision GmbH,
Munich (DE)

( * ) Notice: Subject to any disclaimer, the term of this patent is extended or adjusted under 35 U.S.C. 154(b) by 219 days.

(21) Appl. No.: 12/747,221

(22) PCT Filed: Dec. 12, 2008

(86) PCT No.: PCT/EP2008/067417
§ 371 (c)(1),
(2), (4) Date: Sep. 17, 2010

(87) PCT Pub. No.: WO2009/074676
PCT Pub. Date: Jun. 18, 2009

(65) Prior Publication Data
US 2011/0002514 A1    Jan. 6, 2011

(30) Foreign Application Priority Data
Dec. 13, 2007    (DE) .......................... 10 2007 060 008

(51) Int. Cl.
*G06K 9/00*    (2006.01)
*H01J 3/14*    (2006.01)
*G01N 21/00*    (2006.01)
*A61B 18/18*    (2006.01)

(52) U.S. Cl. ............. 382/128; 250/216; 356/432; 606/5

(58) Field of Classification Search .................. 382/117, 382/128–134; 351/159.07, 159.22, 159.46, 351/159.5, 159.78; 434/262, 267, 271; 606/5, 606/10, 18, 107, 204.25, 356, 400, 401, 558; 250/216; 356/432
See application file for complete search history.

(56) References Cited

U.S. PATENT DOCUMENTS

| | | | | |
|---|---|---|---|---|
| 5,261,822 A * | 11/1993 | Hall et al. | ...................... | 434/271 |
| 5,387,106 A * | 2/1995 | Mackenzie et al. | ........... | 434/271 |
| 5,928,221 A * | 7/1999 | Sasnett et al. | ..................... | 606/5 |
| 6,394,999 B1 * | 5/2002 | Williams et al. | .................. | 606/5 |
| 6,789,900 B2 * | 9/2004 | Van de Velde | ................ | 351/221 |
| 7,537,591 B2 * | 5/2009 | Feige et al. | ..................... | 606/11 |
| 8,182,471 B2 * | 5/2012 | Yee | .................................. | 606/5 |
| 2002/0120198 A1 | 8/2002 | Nakamura | | |

FOREIGN PATENT DOCUMENTS

WO    2009074676 A2    6/2009

* cited by examiner

*Primary Examiner* — Abolfazl Tabatabai
(74) *Attorney, Agent, or Firm* — William Greener; Bond, Schoeneck & King, PLLC

(57) ABSTRACT

The invention relates to an apparatus and a method for determining the energy of a laser. In particular, the invention relates to an initial determination of a laser energy and the monitoring of the laser energy preferably of an excimer laser for use in a refractive laser system for treatment of any eye. An apparatus for determining an energy of an excimer laser comprises a tool comprising an area being ablated with a plurality of laser pulses of said excimer laser using at least one predetermined multi spot ablation pattern, said ablation area comprising a specific ablation area being as large as the ablation area or smaller, an image capturing means for capturing at least one image comprising at least said specific ablation area of the tool; an analyzing means for analyzing said at least one image, wherein the size of the specific ablation area provides a measure of the energy of the excimer laser.

20 Claims, 6 Drawing Sheets

DETERMINATION AND MONITORING OF LASER ENERGY

FIELD OF INVENTION

The invention relates to an apparatus and a method for determining the energy of a laser. In particular, the invention relates to an initial determination of a laser energy and the monitoring of the laser energy preferably of an excimer laser for use in a refractive laser system for treatment of any eye.

BACKGROUND OF THE INVENTION

For the initial determination of a laser energy of a refractive laser systems usually a disposable energy calibration tool is used. This calibration tool consists of a glued foil on top of a coloured base plate. A laser system with nominal fluence level (expressed in $mJ/cm^2$) will penetrate the foil with a specified number of pulses having two target positions on the tool. To test a laser system the number of laser pulses necessary to penetrate the foil is counted and the user determines when the foil is ablated, i.e., the coloured base plate is visible.

Modifications of such base plates are known, e.g., from U.S. Pat. No. 5,464,960 to Deborah K. Hall as laser calibration device. The laser calibration device for calibrating surgical lasers is formed by superimposition of thin-films of alternating colours. After ablation by a laser beam, the resulting spherical cavity appears as a pattern of nested circles whose concentricity and spacing reflect the alignment and intensity of the laser beam. These patterns can be visually or instrumentally analyzed to determine the proper setting of the laser. A monolayer or multi-layer thin film is used to determine not only the ablative power of a laser beam, but also the variation of the ablative power over the full breadth of the beam by observing the area impinged by the beam between successive laser pulses.

The determined number of shots necessary to ablate the foil and thus causing a colour change observed by a user may vary depending on the users subjective perception.

U.S. Pat. No. 7,211,078 relates to a device for monitoring the energy and/or position of a pulsed and scanned laser beam, wherein the pulsed laser beam is intermittently directed at a sensor. The measuring of laser energy and in particular the monitoring of laser energy is accomplished by using optical photodiodes, pyroelectric or thermoelectric sensors. In particular, the laser energy is monitored during operation by measuring a divided part of the laser beam. Alternatively, the entire undivided beam can be deflected onto a sensor.

An aspect of the invention is to improve laser energy measurement and monitoring. In particular, it is an object of the invention to improve the laser energy measurement and monitoring via sensors. A further aspect of the invention is to provide a more objective measurement utilizing a laser calibration tool in order to improve the measurement accuracy.

SUMMARY

The above objects are achieved by the features of the claims. Aspects of the invention are directed to the determination, calibration and monitoring of a laser beam in view of its energy, energy distribution, position and shape.

A first aspect of the invention is directed to an apparatus and a corresponding method for determining an energy of an excimer laser by the use of a tool. The tool comprises an area which is ablated by an excimer laser. The ablation pattern is at least one multi spot ablation pattern, i.e., the ablation is formed by a plurality of laser pulses having different target positions on the tool, wherein the size of one laser pulse is smaller than the ablation pattern. In addition, the tool may also comprise single and/or double spot ablation pattern. The plurality of laser pulses of the multi spot ablation pattern may overlap at least partially with one another. The ablation area of the multi spot ablation pattern comprises a specific ablation area on the tool, which may have the same size as the ablation area or a smaller size. The size of the specific ablation area on the tool is analyzed and the energy of the excimer laser is determined based on the size of the specific ablation area. This analysis is conducted using an image comprising at least said specific ablation area.

The tool comprises at least two layers having different optical characteristics, e.g., different reflective, transmissive, absorption, colour, colour saturation, lightness characteristics. The two layers may be formed of a base plate having a planar upper surface on which a foil is located. A laser beam ablates first the foil.

An image capturing means for obtaining the image/the images to be analyzed may be one of a camera, colour camera, video camera, colour video camera. Said analysis for determining the size of the specific ablation area may based on optical differences of the layers of the tool. Said analysis may be based on the optical characteristics of one specific layer of the tool.

The apparatus for determining an energy of an excimer laser may be incorporated in a laser treatment apparatus. It can be used in intervals, for example before a treatment of a patient's eye or once a day.

A further aspect of the invention relates to an apparatus for laser energy calibration and/or monitoring comprising at least one detection means for detecting a laser beam. Further, the apparatus comprises an evaluation means for evaluating the laser beam energy based on the data output of the detection means. The detection means may be any device suitable to determine the laser beam characteristic. It may comprise at least one optical element, which is located in the laser beam path during normal operation, e.g., during a surgical treatment.

This optical element may be any means located in the laser beam path for transmitting and/or forming and/or focusing and/or reflecting the laser beam, e.g., a lens or a mirror. The optical element comprises material providing at least one of an photoelectric, thermoelectric and pyroelectric effect. The optical element shall be suitable to determine the laser beam characteristics. The optical element comprises such a material to an extent that the optical characteristics of the optical element, i.e. reflective and/or transmissive characteristics, are substantially not deteriorated. In particular, the material is located in such a quantity and location that the laser beam characteristics, e.g., energy and shape are substantially not changed. The material may be connected via electrical conductors such as conductive wires to provide an output signal to any analyzing means in response to for example a pyroelectric effect.

The optical element can be used for continuously monitoring laser energy of a part of the laser beam or the whole laser beam. An erroneous function of the laser system either in position or energy may therefore be detected during the treatment of a patient's eye.

BRIEF DESCRIPTION OF THE DRAWINGS

Illustrative, non-limiting embodiments of the present invention will be described by way of example with reference to the accompanying drawings, in which the same reference number is used to designate the same or similar components in different figures, and in which:

FIG. 10b is a diagram showing the detected energy in correspondence with FIG. 10a.

DETAILED DESCRIPTION

Figure 1A:
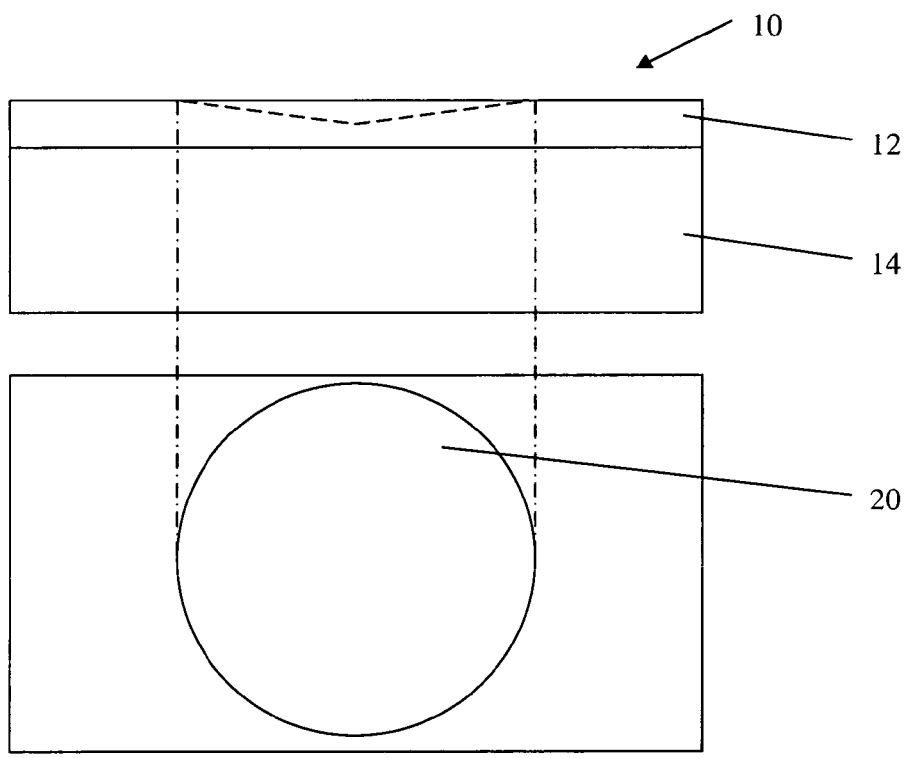
FIGS. 1a, 1b are schematic illustrations of exemplary tools ablated with different laser energy.

The upper part of FIG. 1a shows a cross-section of a tool 10 having a first layer 12 and a second layer 14. The first layer 12 was ablated with a predetermined multi spot ablation pattern having exemplarily a cone like shape. In the case of FIG. 1a the laser energy applied did not form a breakthrough such that the second layer is not visible as illustrated in the lower part of FIG. 1a showing a top view of the tool 10. The top view of the tool 10 shows the ablation area 20 corresponding to the outer circumference of the multi spot ablation pattern as illustrated by the dashed lines.

It is noted that the predetermined multi spot ablation pattern may have various shapes like v-notch, cylindrical, lying cylindrical, a line with gradually increasing/decreasing laser energy, refraction like or any combination thereof. All utilized ablation patterns have a predetermined number of laser pulses. Hence, presuming that the number of laser shots as well as the ablation pattern is predetermined, the depth of penetration of the laser into the tool 10 varies depending on the laser energy.

Figure 1B:
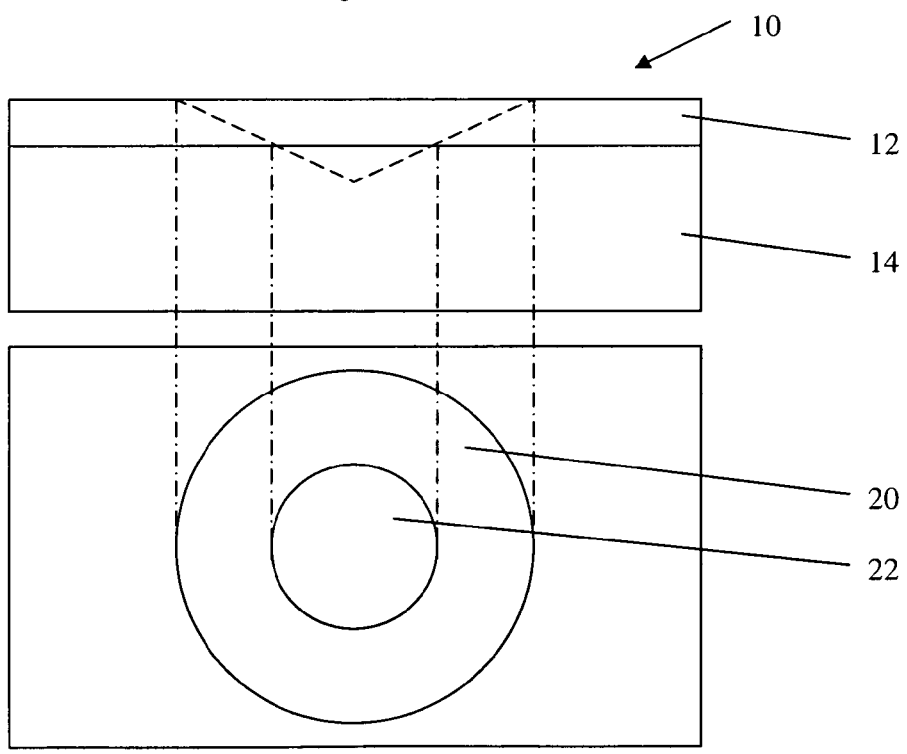

In FIG. 1b the same predetermined multi spot ablation pattern was used for ablating the tool as for the tool shown in FIG. 1a. Thus the same number of laser shots was placed on the predetermined positions on the tool. Due to a higher energy of the laser beam the sum of the energy of all laser pulses created a greater amount of ablation. As a result a cone like shaped ablation pattern was formed in the tool 10, said cone having a greater depth of penetration. The total laser energy applied was sufficient to completely ablate the first layer and to form a breakthrough such that the second layer 14 is visible from the top view of the tool 10. The area wherein the second layer 14 is visible is called the specific ablation area 22. The specific ablation area 22 can be as large as the ablation area 20 or smaller. Due to the fact that the depth of penetration of the laser into the tool 10 is increasing with increasing laser energy, the size of the specific ablation area 22 also increases with increasing laser energy. Therefore, the size of the specific ablation area 22 is a measure for the laser energy.

The first layer of the tool 10 has a predetermined thickness and can be ablated with a predetermined number of laser pulses. The tool 10 may also be formed of more than two layers. Each of the layers may have different optical characteristics like different reflective characteristics and/or colours and/or colour saturations and/or lightness. In particular, abutting layers may have such different characteristics.

Figure 2:
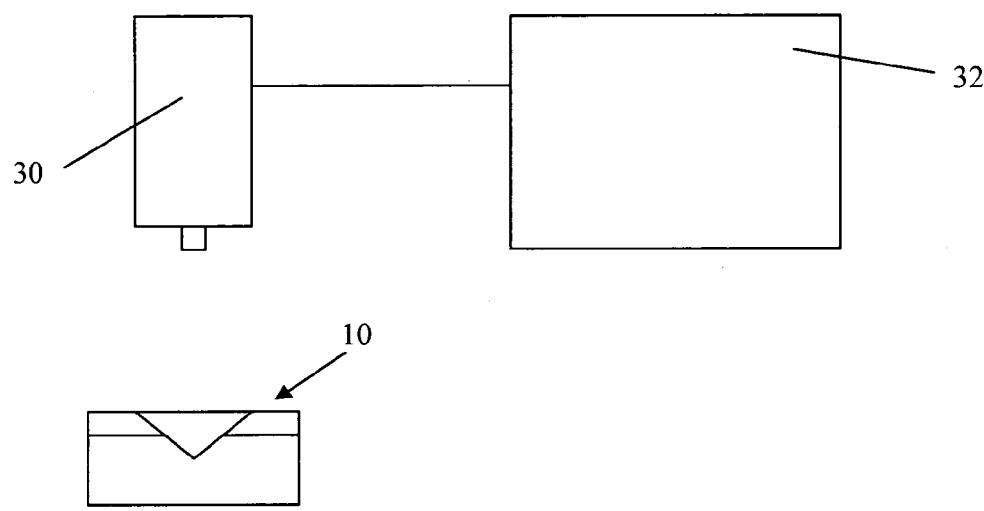
FIG. 2 is a schematic illustration of an apparatus for determining an energy of an excimer laser.

FIG. 2 illustrates an apparatus for determining an energy of an excimer laser according to a first aspect of the invention comprising a camera 30 as an image capturing means and an analyzing means 32 for analyzing the output of the image capturing means. The camera 30 is one of a photo camera and a video camera taking black-and-white or colour pictures/films. Depending on the type of camera the camera 30 captures at least one image or a plurality of images at least comprising the specific ablation area(s) on the tool 10. There may also be more than one image capturing means, particularly in case of having more than one ablation pattern on the tool 10 to be analyzed.

The analyzing means 32 processes the image data output from camera 30. The analyzing means 32 can utilize an image analysis algorithm to analyze differences in at least one of lightness and/or colour and/or colour saturation in the image. In this regard it is noted that the term lightness is used as having the same meaning as the term brightness. In particular, the analyzing means 32 may alter the lightness and/or colour and/or colour saturation value of image pixels to another predetermined lightness and/or colour and/or colour saturation value. An example therefore is that a tool comprises a second layer of red material, which is visible so that an image comprises a certain range of red pixels, e.g., having different colour saturation values which are altered to have one predetermined colour saturation value. Thus, a kind of mapping is performed, wherein every output value has an input value with a certain range in lightness and/or colour and/or colour saturation. This "mapping" can also have other output values, like "relevant"-"not relevant", or "specific ablation area"-"ablation area"-"not relevant" etc.

Figures 3A, 3B, 3C:
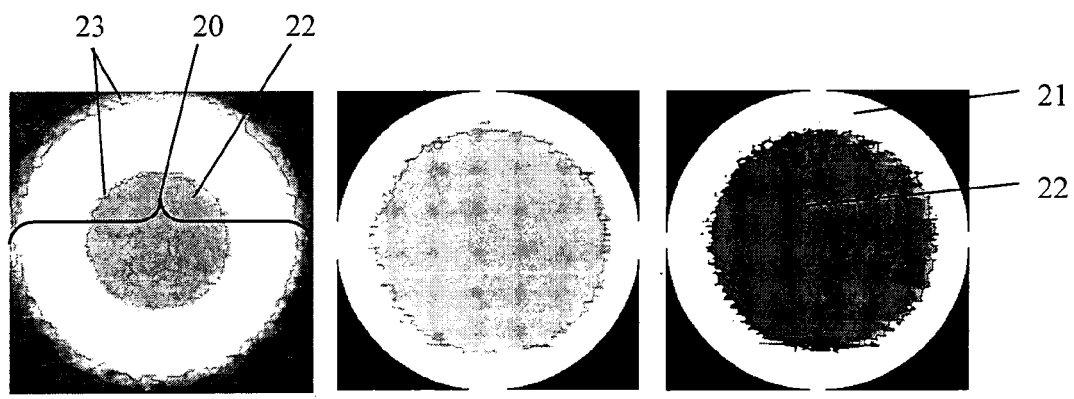
FIGS. 3a, 3b, 3c are exemplary illustrations of an image processing input (FIG. 3a) an intermediate step (FIG. 3b) and an image processing output (FIG. 3c)

FIG. 3a shows an exemplary image data provided by the camera 30. The image comprises at least the specific ablation area 22. In the example as shown in FIG. 3a the image comprises almost the whole ablation area 20. FIG. 3a illustrates transition zones 23 from the specific ablation area 22 to the ablation area 20 and from the ablation area 20 to the first layer 12 of the tool 10. Preferably, only a part of the image, i.e. an analyzed ablation area 21, is analyzed. Therefore, as illustrated in FIG. 3b, the respective part of the image to be analyzed is cut out by software or the like. The analyzed ablation area 21 comprises at least the specific ablation area 22. Also, the whole ablation area 20 may be analyzed. FIG. 3c shows an exemplary image output data after a processing step of the analyzing means 32. In order to clearly differentiate the ablation area 20 or the analyzed ablation area 21 from the specific ablation area 22 the pixels of the image provided by the camera 30 can be analyzed in view of their gray scale value in terms of lightness. Further, similar to the above explained "mapping" example, the lightness of pixels is changed, wherein a pixel having a lightness value greater than a predetermined lightness value, i.e. brighter in appearance, is changed to a white pixel and a pixel having a lightness value smaller than the predetermined lightness value, i.e. darker in appearance, is changed to a grey/dark pixel having a predetermined grey scale value/lightness. As apparent from FIG.

3c, the specific ablation area 22 can then clearly be differentiated from the analyzed ablation area 21.

Referring back to FIG. 2, the analyzing means 32 can then determine the energy of the laser pulses applied for ablating the tool 10. In particular, the analyzing means 32 determines the laser energy based on the size of the specific ablation area 22. Data correlating a size of a reference specific ablation area with a reference laser beam energy may be stored in the analyzing means. This reference specific ablation area is compared with the actual size of the specific ablation area 22. From this comparison the actual laser energy of the laser beam which has formed the ablation as captured by said camera 30 is evaluated. In a first processing step it may only be determined whether the actual laser energy is within a certain range, i.e., whether the size of the specific ablation area is not too small and not to great. If this test is positive any further processing may be omitted. Alternatively, the laser energy may be evaluated in detail. The analyzing means may provide an output for adjusting the energy of a laser source based on the difference of the actual size of the specific ablation area 22 and the size of the reference specific ablation area.

For determining the size of the specific ablation area 22 by the analyzing means 32 the respective part of the image comprising at least the specific ablation area 22 may be cut out, i.e., only a part of the image may be analyzed in order to make the processing more efficient. FIGS. 3b, 3c illustrate a circular cut-out, however, various cut-outs are possible, like a cut-out covering the whole ablation area 20 or a quadrate cut-out. Such a cut-out may be accomplished after capturing of the image as well as before, i.e., by a respective configuration of the camera 30 in relation to the specific ablation area 22 and/or the ablation area 20 or by selecting the relevant data of the image taken by the camera. Also, the whole image provided by the camera 30 may be analyzed. The size of the specific ablation area 22 may be determined in percent in relation to a reference area, the reference area being 100%. Preferably, the reference area is one of the ablation area 20 or the analyzed ablation area 21.

One possibility to distinguish the ablation areas, i.e., to determine the size of the ablation area 20 or the size of the analyzed ablation area 21 and the specific ablation area 22 is to count the number of pixels falling within a predetermined range in lightness and/or colour and/or colour saturation. Knowing the range of the pixels in lightness and/or colour and/or colour saturation corresponding to the specific ablation area 22 its size can be determined. This range in lightness and/or colour and/or colour saturation may be stored in the analyzing means 32 or obtained via a measurement, e.g., in the middle of an ablation area 20. In the latter case it is preferably assured that in fact the reference measurement is taken on a place where the first layer 12 is completely ablated. This may be accomplished by the analyzing means by conducting a validity check. The total number of counted pixels represents a certain area of the image, e.g., the analyzed ablation area 21. Thus, the percental size of the specific ablation area 22 can be determined relative to the analyzed ablation area 21. Also the number of counted pixel relating to the specific ablation area can be correlated directly to the energy of the laser. Due to the fact that the ablation pattern(s) have a predetermined, i.e. known, number of shots also the mean energy of each laser shot can be determined.

Figure 4A:
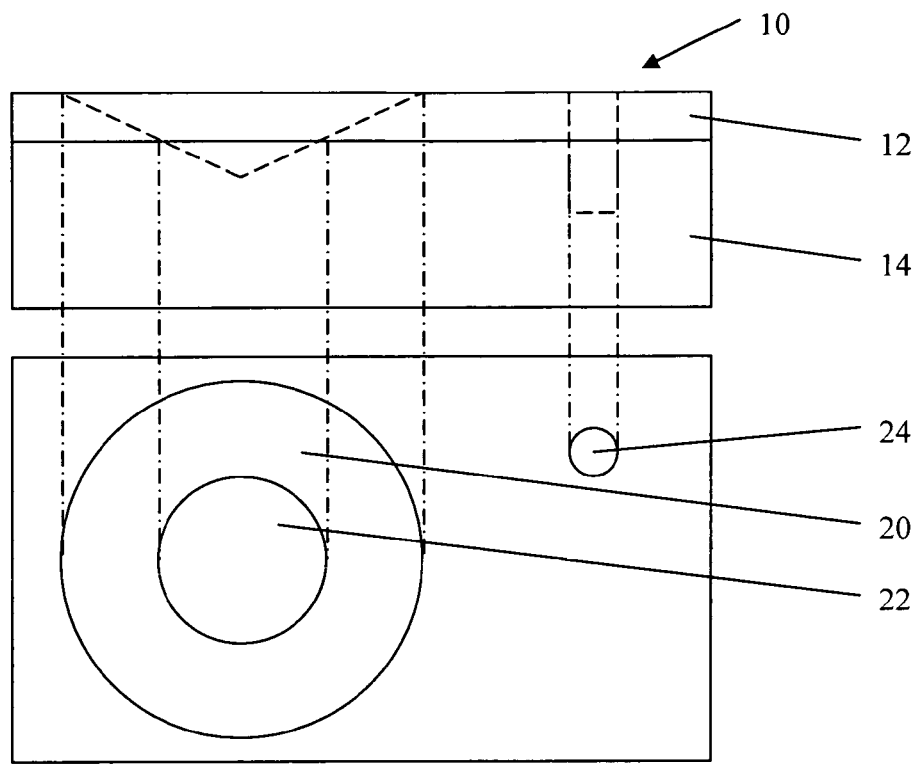
FIG. 4a is a schematic illustration of an ablation tool comprising two ablations.

As illustrated in FIG. 4a also more than one ablation may be formed in the tool 10 and analyzed according to the invention. The single spot ablation area 24 is formed by more laser pulses aimed at the same position on the tool 10. This single spot ablation area 24 may be formed during the formation of the multi spot ablation pattern, exemplarily illustrated as having a cone like shape. A predetermined number of laser pulses may be directed away from the multi spot ablation pattern to form the single spot ablation area 24, e.g., in certain intervals. This is advantageous since the function and accuracy of the laser scanning system, i.e. the correct beam deflection, can be checked. Also, since the single spot ablation is formed by laser pulses aimed at the same position on the tool 10, the laser spot diameter can be determined/verified. This, however, presumes that the laser scanner works correctly, i.e., within a certain accuracy. The two ablation areas 20 and 24 may be formed by a different number of laser pulses. The results from the single spot ablation can be used to check the applicability of the multi spot ablation pattern, i.e., in case the characteristics of the ablation area 24 do not correspond to a stored reference, which is preferably an ablation area 24 made without movement of the laser scanning system, it may be concluded that also the multi spot ablation pattern is incorrect. A failure may be caused, e.g., by a defective laser scanner system, wrong focus, ground motion, vibration etc.

Figure 4B:
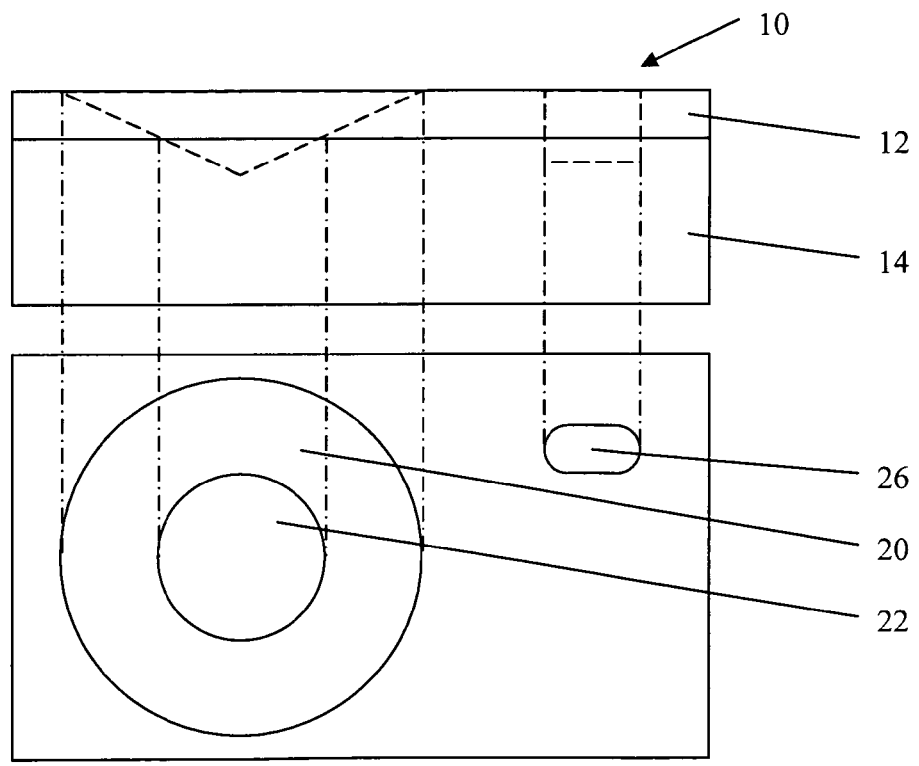
FIG. 4b is a schematic illustration of an ablation tool comprising an faulty ablation.

FIG. 4b illustrates two ablation patterns like FIG. 4a, however, single spot ablation area 26 is not correctly formed. One possibility for such an ablation pattern is a scanner defect. In this case also the multi spot ablation pattern may show certain deviations (not shown) particularly in the circumference of ablation area 20 or specific ablation area 22. As explained above in view of the multi spot ablation area also the single spot ablation area can be analyzed, e.g., the pixel falling within a predetermined range in lightness and/or colour and/or colour saturation corresponding to the single spot ablation area may be counted to determine the size of the ablation area. Alternatively to the single spot ablation area, also a double spot ablation area or an ablation area with more than two ablation target positions on the tool 10 may be employed for determining the characteristics of the laser beam and/or the scanner.

It is noted that in the upper part of FIG. 4b the single spot ablation area 26 is illustrated as planar, however, with a laser scanner defect or a vibration during the formation of the single spot ablation area 26 it may occur that the ablation depth in the peripheral zone is less then the central zone.

Figure 5:
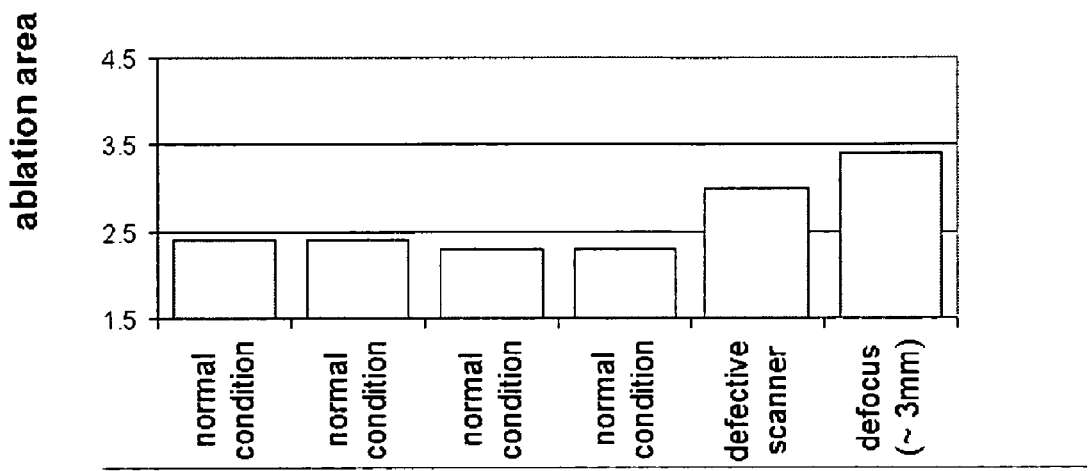
FIG. 5 is a diagram illustrating the size of an ablation area of a single shot ablation pattern under different conditions.

In FIG. 5 the ablation area for a single spot ablation is shown under different conditions. The ablation area is given in arbitrary units (a.u.). As can be taken from the first four bars (starting from left), there may be a certain range under which the laser is expected to work correctly. The fifth bar relates to an exemplary scanner defect. The ablation area significantly increases, however, this may vary depending on the extent of the scanner defect. The sixth bar illustrates the ablation area with a defocus of 3 mm. This means that the point of focus is 3 mm in depth away from the surface to be ablated.

Figure 6:
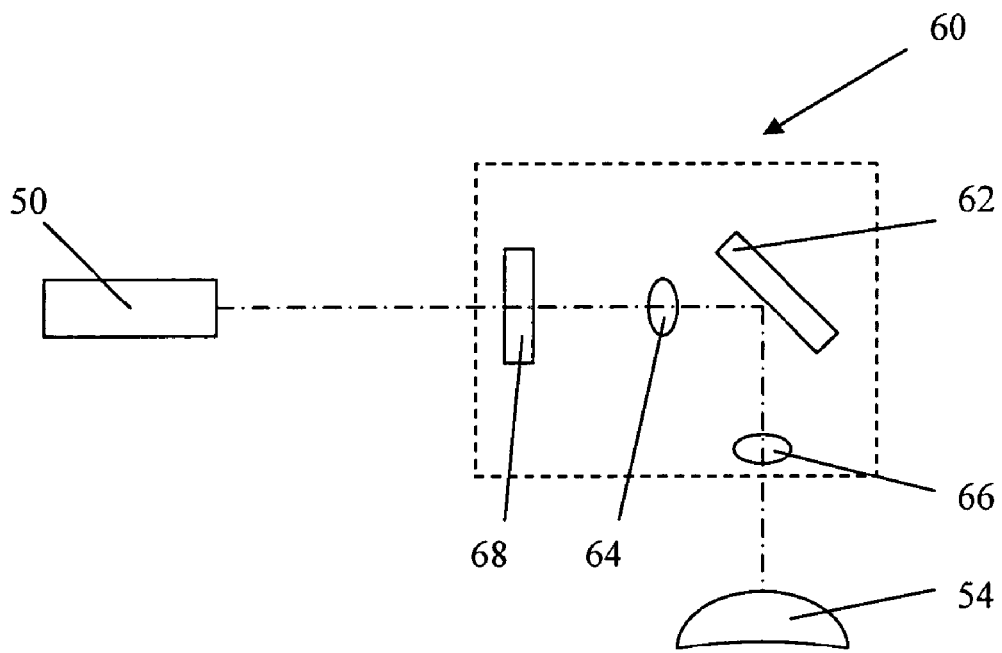
FIG. 6 is a schematic illustration of an apparatus for laser energy calibration and/or monitoring.

A further aspect of the invention, illustrated in a schematic drawing in FIG. 6, relates to an apparatus for laser energy calibration and/or monitoring 60. This apparatus 60 comprises at least one detection means, which can detect a laser pulse. The detection means can determine the energy of a laser pulse and comprises at least one optical element which is located in the laser beam path. For the sake of completeness, FIG. 6 also shows a laser source 50 and a target object 54, like a calibration tool 10 or a patient's eye to be treated.

The detection means can be realized as an optical element having reflective and/or transmissive characteristics, i.e. as an integral part of the optical element and/or as a layer on or within the optical element. In particular, the optical element may be a mirror 62, e.g. a scanner mirror for deflecting the laser beam during a treatment, and/or a lens 64, 66. The optical element having the detection capability may be advantageously provided close to the laser source 50 and/or close to the target 54, i.e., as the last optical element in the beam path before the target.

In an aspect, an optical element comprises both optical material, contributing to the optical characteristics, and measurement material, providing a measurement signal. The measurement material provides a thermoelectrical and/or pyroelectrical effect and can be electrically connected, e.g., via a grid of electrical conductors formed on and/or within the optical element. The measurement material, which may not contribute to the optical characteristic of the optical element is provided to such an extent and in such a location/distribution over the optical element to substantially not deteriorate or only to a certain extent the optical characteristics. It is preferred that the measurement material and/or the respective connecting elements are not visible/detectable in the image plane of the laser pulse.

Further, the apparatus 60 may comprise a comparison means for comparing an actual measurement of the detection means with a previous measurement of the detection means for monitoring the laser beam quality. Instead of a previous measurement or in addition a measurement by using a standardized light source can be used. The standardized light source may also be used for checking and/or calibrating the detection means.

Figure 7A:
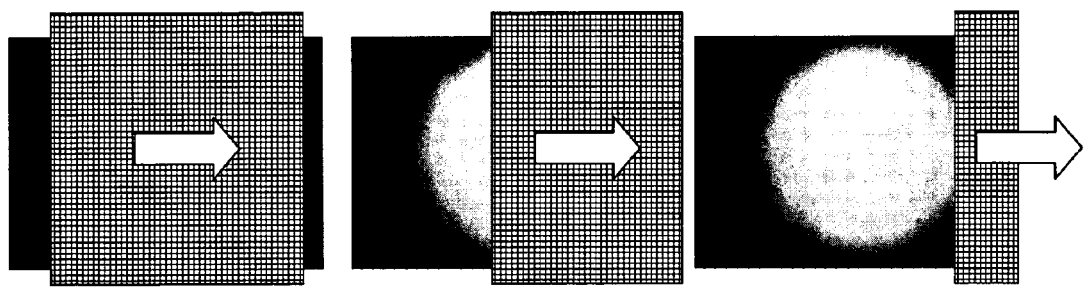
FIG. 7a is a schematic illustration of a mask moving transverse to an axis of a laser beam.
Figure 7B:
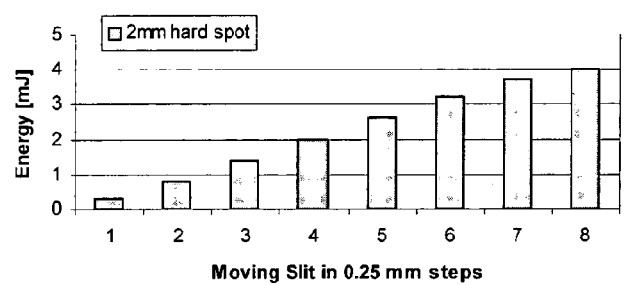
FIG. 7b is a diagram showing the detected energy during movement of a slit mask transverse to an axis of a laser beam.

The apparatus 60 may also comprise a mask 68 located in front of the detection means for selectively blocking at least a part of the laser beam from the detection means. The mask 68 may be a slit mask, which is laterally moved transverse to the axis of the laser beam. According to an aspect the slit mask is moved at least from one edge of the laser beam to the opposite edge. The moving of a slit mask may be accomplished with help of a stepper motor. FIG. 7a shows an exemplary mask, which initially shadows the complete laser beam and moves gradually away or stepwise in the direction of the arrow, i.e. to the right hand side in the Figure. In FIG. 7b the energy distribution is illustrated for eight different positions of a slit mask moved in steps of 0.25 mm. As can be seen from the diagram, a 2 mm hard spot was used and 8 measurements have been taken. The measurements show that the increase of the circle shaped laser spot does not increase in a linear manner, but has a s-shape. This is due to the fact that in the first and the last measurements only a relatively little energy change is measured. This measurement data can be compared to reference values and thus both the total energy of the laser beam as well as the energy distribution can be measured. In this way also a misalignment of the laser can be detected.

Figures 8A, 8B:
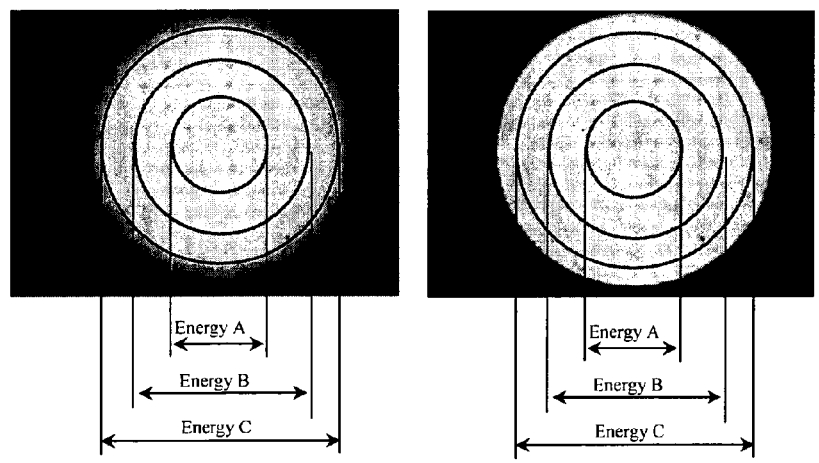
FIGS. 8a, 8b are illustrations of measurement zones of a soft spot/hard spot laser beam.
Figure 9:
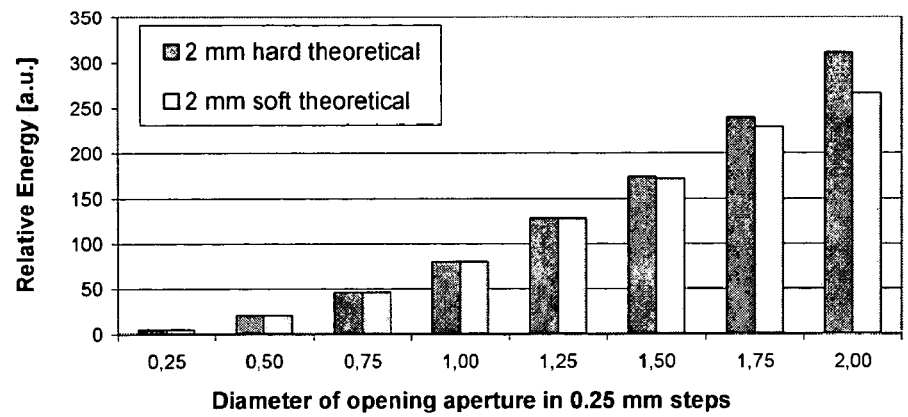
FIG. 9 is a diagram showing the theoretical energy in correspondence with FIGS. 8a, 8b for different spot shapes.

The mask 68 may also be an iris diaphragm with an adjustable opening diameter. A laser spot energy distribution can then be determined from the center of the beam to the peripheral zone or vice versa. As illustrated in FIG. 8, the iris diaphragm may have a certain number of opening positions to detect the laser energy in the respective aperture. FIG. 8a illustrates a soft spot laser beam and FIG. 8b a hard spot laser beam. The respective theoretical energy distribution is shown in FIG. 9, the x-axis relating to the opening diameter of the iris diaphragm and the y-axis relating to the relative energy in arbitrary units (a.u.) detected by the detection means. An energy measurement is accomplished every 0.25 mm from 0 mm to 2 mm. The left part of each bar shows the energy of a 2 mm hard spot and the right part of a 2 mm soft spot. As can be taken from the measurement values the soft spot has a decreasing energy in the peripheral zone in comparison to the hard spot. This becomes apparent particularly from the last three bars.

The mask 68 may also comprise an aperture having a cake piece like cut out (not illustrated), which is gradually or stepwise rotated about an axis of rotation. The energy can be detected similar to the above explained examples by taking measurements at different angular positions of the mask. Also a combination of more mask types may be applied to measure different energy distributions of the laser beam across the area of the laser beam.

With the mask 68 it is possible to measure the beam quality, e.g., beam shape and energy distribution. For each mask position the specific energy of the laser pulse is measured and can be compared with a previous measurement or a reference measurement. For processing the measurement data of the detection means, the apparatus 60 may comprise a homogeneity check means, comparing the mask location/opening dependent energy output of the detection means with a stored energy value for evaluating the beam homogeneity.

Figure 10A:
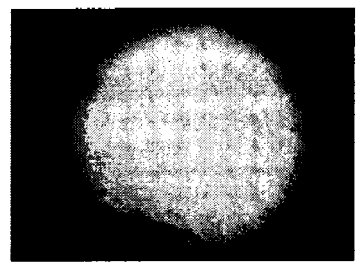
FIG. 10a illustrates a soft spot laser beam with an edge defect.
Figure 10B:
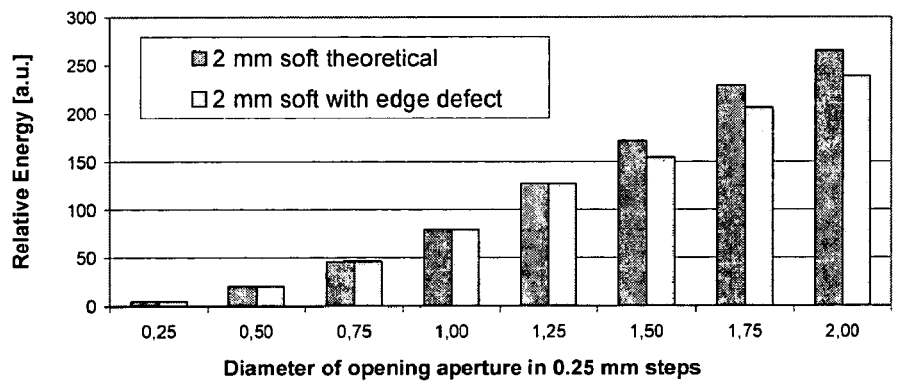

In FIG. 10a a soft spot laser beam with an edge defect is illustrated. FIG. 10b shows the corresponding energy distribution of both a theoretical energy target value and the measured energy value. The edge defect causes a difference only in the last three opening diameters, starting the measurement with a small iris diaphragm opening diameter, i.e., in the peripheral zone of the laser beam.

It is noted that the above described apparatus for determining an energy of an excimer laser utilizing a tool 10 and the apparatus for laser energy calibration and/or monitoring 60 may be separately or together incorporated into a laser treatment system. In the latter case the determined energy and/or laser beam characteristics may be compared or at least one output may serve as a reference.

While certain embodiments have been chosen to illustrate the invention it will be understood by those skilled in the art that changes and modifications can be made therein without departing from the scope of the invention as defined in the appended claims.

The invention claimed is:

1. An apparatus for determining the energy of a laser, comprising:
    a tool including a base layer and at least one additional layer disposed immediately adjacent the base layer, wherein the base layer and the at least one additional layer are each characterized by a material that is ablatable by a laser beam, further wherein at least a portion of the at least one additional layer provides an ablation area to be ablated by a multi-spot ablation pattern from a laser and at least a portion of the base layer provides a specific ablation area to be ablated by the multi-spot ablation pattern that will be equal to or less than the ablation area, further wherein the specific ablation area will provide an indicia of the energy of the laser.

2. The apparatus of claim 1, further comprising:
    an image capture component disposed to capture an image of the ablation area and the specific ablation area; and
    an analyzer component disposed to receive image data from the image capture component and use at least the received image data to determine the laser energy.

3. The apparatus of claim 1, wherein the at least one additional layer has a predetermined thickness that can be ablated-through with a predetermined number of known laser pulses.

4. The apparatus of claim 1, wherein the base layer and the at least one additional layer are characterized by different optical characteristics including at least one of reflective characteristics, colours, colour saturation, and lightness.

5. The apparatus of claim 2, wherein the analyzer component includes stored data correlating a size of a reference specific ablation area with a reference laser beam energy.

6. The apparatus of claim 1, wherein a different portion of the at least one additional layer provides a second ablation area to be ablated by one of a single-spot and a double-spot ablation pattern from the laser and a different portion of the base layer provides a second specific ablation area to be ablated by the one of a single-spot and a double-spot ablation pattern from the laser.

7. The apparatus of claim 1, further comprising a therapeutic laser treatment apparatus coupled thereto.

8. A method for determining the energy of a laser, comprising:

capturing at least one image of at least a specific ablation area on a tool, wherein the specific ablation area is equal to or smaller than an ablation area on the tool and, which is contained within a circumferential boundary of the ablation area; and analyzing the at least one image, wherein the size of the specific ablation area is an indicia of the energy of the laser.

9. The method of claim 8, wherein the analyzing step further comprises analyzing a difference in at least one of lightness, colour, and colour saturation in the image of the at least a specific ablation area.

10. The method of claim 8, wherein the analyzing step further comprises determining a percentage of the specific ablation area in relation to a reference area, the reference area being 100%.

11. The method of claim 8, wherein the analyzing step further comprises counting pixels falling within a predetermined range in lightness and/or colour and/or colour saturation, corresponding to the specific ablation area.

12. The method of claim 8, wherein the analyzing step further comprises correlating a size of a reference specific ablation area with a reference laser beam energy and determining the energy of the laser beam based on the size of the specific ablation area.

13. The method of claim 8, wherein the analyzing step further comprises counting the number of pixels falling within a predetermined range in lightness and/or colour and/or colour saturation corresponding to the specific ablation area.

14. The method of claim 8, wherein the analyzing step further comprises evaluating a laser spot diameter based on a second ablation area formed by one of a single spot ablation pattern and a double spot ablation pattern on the tool.

15. An apparatus for laser energy calibration and/or monitoring, comprising:

a laser beam detection component; and a laser beam evaluation component that utilizes an output from the laser beam detection component, wherein the detection component includes at least one optical element disposed to intercept at least a portion of the laser beam, further wherein the optical element comprises one of a material and a component that provides one of a thermoelectrical effect and a pyroelectrical effect.

16. The apparatus of claim 15, wherein the optical element is one of optically reflective and transmissive.

17. The apparatus of claim 15, wherein the optical element includes a grid of electrical conductors formed on and/or in the thermoelectrical and/or pyroelectrical material or component.

18. The apparatus of claim 15, further comprising a comparison means for comparing an actual measurement of the detection component with a previous measurement of the detection component for monitoring the laser beam.

19. The apparatus of claim 15, further comprising a mask disposed in front of the detection component for selectively blocking at least a part of the laser beam from the detection component.

20. The apparatus of claim 15, further comprising a therapeutic laser treatment apparatus coupled thereto.

* * * * *